US006828299B2

(12) United States Patent
Yang et al.

(10) Patent No.: US 6,828,299 B2
(45) Date of Patent: Dec. 7, 2004

(54) POLYHYDROXY GLYCOPEPTIDE DERIVATIVES

(75) Inventors: Guang Yang, San Mateo, CA (US); Donald E. Schmidt, Jr., Brisbane, CA (US); J. Kevin Judice, El Granada, CA (US)

(73) Assignee: Theravance, Inc., South San Francisco, CA (US)

( * ) Notice: Subject to any disclaimer, the term of this patent is extended or adjusted under 35 U.S.C. 154(b) by 450 days.

(21) Appl. No.: 09/847,061

(22) Filed: May 1, 2001

(65) Prior Publication Data

US 2002/0049156 A1 Apr. 25, 2002

Related U.S. Application Data

(60) Provisional application No. 60/213,428, filed on Jun. 22, 2000.

(51) Int. Cl.[7] .............................. A61K 38/16; C07K 1/00
(52) U.S. Cl. .............................. 514/8; 514/11; 530/317; 530/395; 530/322
(58) Field of Search .................. 514/8, 11; 530/317, 530/322, 395

(56) References Cited

U.S. PATENT DOCUMENTS

| | | | |
|---|---|---|---|
| 4,643,987 A | 2/1987 | Nagarajan et al. | 514/8 |
| 4,698,327 A | 10/1987 | Nagarajan et al. | 514/8 |
| 4,727,064 A | 2/1988 | Pitha | 514/58 |
| 4,983,586 A | 1/1991 | Bodor | 514/58 |
| 5,024,998 A | 6/1991 | Bodor | 514/58 |
| 5,591,714 A | 1/1997 | Nagarajan et al. | 514/9 |
| 5,602,112 A | 2/1997 | Rubinfeld | 514/58 |
| 5,750,509 A | 5/1998 | Malabarba et al. | 514/11 |
| 5,840,684 A | 11/1998 | Cooper et al. | 514/11 |
| 5,916,873 A | 6/1999 | Cooper et al. | 514/9 |

FOREIGN PATENT DOCUMENTS

| | | | |
|---|---|---|---|
| EP | 0667353 | 8/1995 | C07K/9/00 |
| EP | 0816378 | 1/1998 | C07K/9/00 |
| WO | WO 94/12217 | 6/1994 | |
| WO | 00/04044 | 1/2000 | C07K/7/50 |
| WO | 00/39156 | 7/2000 | C07K/9/00 |
| WO | WO-00/54751 | 9/2000 | |
| WO | 00/59528 | 10/2000 | A61K/38/08 |
| WO | WO-01/83520 | 11/2001 | |
| WO | WO-01/98326 | 12/2001 | |
| WO | WO-01/98327 | 12/2001 | |
| WO | WO-01/98328 | 12/2001 | |
| WO | WO-01/97851 | 3/2002 | |

OTHER PUBLICATIONS

Zang, M., et al., "A review of recent applications of cyclodextrins for drug discovery", *Expert Opinion on Therapeutic Patents*, 9 (12), 21 p., (1999).

Allen, N.E., et al., "The Role of Hydrophobic Side Chains as Determinants of Antibacterial Activity of Semisynthetic Giycopeptide Antibiotics", *The Journal of Antobiotics*, 50 (8), pp. 677–684, (Aug. 1997).

Ge, M., et al., "Vancomycin Derivatives That Inhibit Peptidoglycan Biosynthesis Without Binding", *Science*, 284, pp. 507–511, (Apr. 16, 1999).

Nagarajan, R., et al., "Synthesis and Antibacterial Evaluation of N–Alkyl Vancomycins", *The Journal of Antibiotics*, XLII (1), pp. 63–72, (Jan. 1989).

Nicolaou, K.C., et al., "Chemistry, Biology, and Medicine of the Glycopeptide Antibiotics", *Angew. Chem. Int. Ed.*, 38, pp. 2097–2152, (1999).

Pavlov, A.Y., et al., "A New Type of Chemical Modification of Glycopeptides Antibiotics: Aminomethylated Derivatives of Eremomycin and Their Antibacterial Activity", *The Journal of Anitbiotics*, 50 (6), pp. 509–513, (Jun. 1997).

Pavalov, A.Y., et al., "Chemical Modification of Glycopeptide Antibiotics [VC1]", *Russian Journal of Bioorganic Chemistry*, 24 (9), pp. 570–587, (1998).

Pavlov, A.Y., et al., "Mono and Double Modified Teicoplanin Aglycon Derivaties on the Amino Acid No. 7; Structure–activity Relationsip", *The Journal of Antibiotics*, 51 (1), pp. 73–78, (Jan. 1998).

Primary Examiner—Karen Cochrane Carlson
Assistant Examiner—Samuel W. Liu
(74) Attorney, Agent, or Firm—Jeffrey A. Hagenah

(57) ABSTRACT

Disclosed are polyhydroxy derivatives of glycopeptides and pharmaceutical compositions containing such glycopeptide derivatives. The disclosed glycopeptide derivatives are useful as antibacterial agents.

16 Claims, No Drawings

POLYHYDROXY GLYCOPEPTIDE DERIVATIVES

PRIORITY OF INVENTION

This application claims priority to U.S. Provisional Application No. 60/213,428, filed Jun. 22, 2000, which application is incorporated herein by reference in its entirety.

BACKGROUND OF THE INVENTION

1. Field of the Invention

This invention is directed to novel polyhydroxy derivatives of glycopeptide antibiotics and related compounds. This invention is also directed to pharmaceutical compositions containing such polyhydroxy glycopeptide derivatives, methods of using such polyhydroxy glycopeptide derivatives as antibacterial agents, and processes and intermediates useful for preparing such polyhydroxy glycopeptide derivatives.

2. Background

Glycopeptides (e.g. dalbaheptides) are a well-known class of antibiotics produced by various microorganisms (see *Glycopeptide Antibiotics,* edited by R. Nagarajan, Marcel Dekker, Inc. New York (1994)). These complex multi-ring peptide compounds are very effective antibacterial agents against a majority of Gram-positive bacteria. Although potent antibacterial agents, the glycopeptides antibiotics are not used in the treatment of bacterial diseases as often as other classes of antibiotics, such as the semi-synthetic penicillins, cephalosporins and lincomycins, due to concerns regarding toxicity.

In recent years, however, bacterial resistance to many of the commonly-used antibiotics has developed (see J. E. Geraci et al., *Mayo Clin. Proc.* 1983, 58, 88–91; and M. Foldes, *J. Antimicrob. Chemother.* 1983, 11, 21–26). Since glycopeptide antibiotics are often effective against these resistant strains of bacteria, glycopeptides such as vancomycin have become the drugs of last resort for treating infections caused by these organisms. Recently, however, resistance to vancomycin has appeared in various microorganisms, such as vancomycin-resistant enterococci (VRE), leading to increasing concerns about the ability to effectively treat bacterial infections in the future (see Hospital Infection Control Practices Advisory Committee, *Infection Control Hospital Epidemiology,* 1995, 17, 364–369; A. P. Johnson et al., *Clinical Microbiology Rev.,* 1990, 3, 280–291; G. M. Eliopoulos, *European J Clinical Microbiol., Infection Disease,* 1993, 12, 409–412; and P. Courvalin, *Antimicrob. Agents Chemother,* 1990, 34, 2291–2296).

A number of derivatives of vancomycin and other glycopeptides are known in the art. For example, see U.S. Pat. Nos. 4,639,433; 4,643,987; 4,497,802; 4,698,327; 5,591,714; 5,840,684; and 5,843,889. Other derivatives are disclosed in EP 0 802 199; EP 0 801 075; EP 0 667 353; WO 97/28812; WO 97/38702; WO 98/52589; WO 98/52592; and in *J. Amer. Chem. Soc.,* 1996, 118, 13107–13108; *J. Amer. Chem. Soc.,* 1997, 119, 12041–12047; and *J. Amer. Chem. Soc.,* 1994, 116, 4573–4590.

Despite the above referenced disclosures, a need currently exists for novel glycopeptide derivatives having effective antibacterial activity and an improved mammalian safety profile. In particular, a need exists for glycopeptide derivatives which are effective against a wide spectrum of pathogenic microorganisms, including vancomycin-resistant microorganisms, and which have reduced tissue accumulation and/or nephrotoxicity.

SUMMARY OF THE INVENTION

The present invention provides novel polyhydroxy glycopeptide derivatives having highly effective antibacterial activity and an improved mammalian safety profile. More specifically, the polyhydroxy glycopeptide derivatives of the invention unexpectedly exhibit reduced tissue accumulation and/or nephrotoxicity when administered to a mammal.

Accordingly, the invention provides a compound of the invention, which is a glycopeptide of formula I:

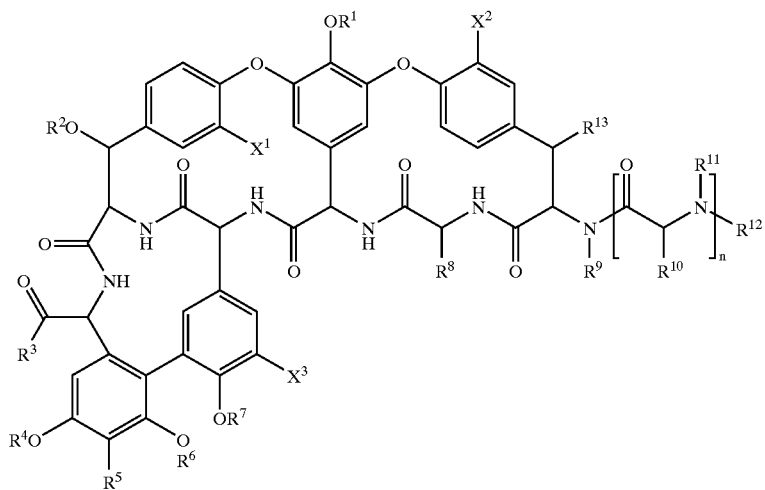

(I)

wherein:

$R^1$ is an amino containing saccharide group substituted on the amine with a substituent that comprises two or more (e.g. 2, 3, 4, 5, or 6) hydroxy (OH) groups;

$R^2$ is hydrogen or a saccharide group optionally substituted with —$R^a$—Y—$R^b(Z)_x$, $R^f$, —C(O)$R^f$, —C(O)$R^f$, or —C(O)—$R^a$—Y—$R^b$—$(Z)_x$;

$R^3$ is —$OR^c$, —$NR^cR^c$, —O—$R^a$—Y—$R^b$—$(Z)_x$, —$NR^c$—$R^a$—Y—$R^b$—$(Z)_x$, —$NR^cR^e$, or —O—$R^e$;

R⁴ is selected from the group consisting of hydrogen, alkyl, substituted alkyl, alkenyl, substituted alkenyl, alkynyl, substituted alkynyl, —R$^a$—Y—R$^b$—(Z)$_x$, —C(O)R$^d$ and a saccharide group optionally substituted with —R$^a$—Y—R$^b$—(Z)$_x$, R$^f$, —C(O)R$^f$, or —C(O)—R$^a$—Y—R$^b$—(Z)$_x$;

R⁵ is selected from the group consisting of hydrogen, halo, —CH(R$^c$)—NR$^c$R$^c$, —CH(R$^c$)—NR$^c$R$^c$, —CH(R$^c$)—NR$^c$—R$^a$—Y—R$^b$—(Z)$_x$, —CH(R$^c$)—R$^x$, and —CH(R$^c$)—NR$^c$—R$^a$—C(=O)—R$^x$;

R⁶ is selected from the group consisting of hydrogen, alkyl, substituted alkyl, alkenyl, substituted alkenyl, alkynyl, substituted alkynyl, —R$^a$—Y—R$^b$—(Z)$_x$, —C(O)R$^d$ and a saccharide group optionally substituted with —NR$^c$—R$^a$—Y—R$^b$—(Z)$_x$, or R⁵ and R⁶ can be joined, together with the atoms to which they are attached, form a heterocyclic ring optionally substituted with —NR$^c$—R$^a$—Y—R$^b$—(Z)$_x$;

R⁷ is selected from the group consisting of hydrogen, alkyl, substituted alkyl, alkenyl, substituted alkenyl, alkynyl, substituted alkynyl,—R$^a$—Y—R$^b$—(Z)$_x$, and —C(O)R$^d$;

R⁸ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R⁹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R¹⁰ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or R⁸ and R¹⁰ are joined to form —Ar¹—O—Ar²—, where Ar¹ and Ar² are independently arylene or heteroarylene;

R¹¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or R¹⁰ and R¹¹ are joined, together with the carbon and nitrogen atoms to which they are attached, to form a heterocyclic ring;

R¹² is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, —C(NH)NR$^c$R$^c$ and —R$^a$—Y—R$^b$—(Z)$_x$, or R¹¹ and R¹² are joined, together with the nitrogen atom to which they are attached, to form a heterocyclic ring;

R¹³ is selected from the group consisting of hydrogen or —OR¹⁴;

R¹⁴ is selected from hydrogen, —C(O)R$_d$ and a saccharide group;

each R$^a$ is independently selected from the group consisting of alkylene, substituted alkylene, alkenylene, substituted alkenylene, alkynylene and substituted alkynylene;

each R$^b$ is independently selected from the group consisting of a covalent bond, alkylene, substituted alkylene, alkenylene, substituted alkenylene, alkynylene and substituted alkynylene, provided R$^b$ is not a covalent bond when Z is hydrogen;

each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R$^e$ is a saccharide group;

each R$^f$ is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic;

R$^x$ is a nitrogen-linked amino saccharide or a nitrogen-linked heterocycle;

X¹, X² and X³ are independently selected from hydrogen or chloro;

each Y is independently selected from the group consisting of oxygen, sulfur, —S—S—, —NR$^c$—, —S(O)—, —SO₂—, —NR$^c$C(O)—, —OSO₂—, —OC(O)—, —NR$^c$SO₂—, —C(O)NR$^c$—, —C(O)O—, —SO₂NR$^c$—, —SO₂O—, —P(O)(OR$^c$)O—, —P(O)(OR$^c$)NR$^c$—, —OP(O)(OR$^c$)O—,—OP(O)(OR$^c$)NR$^c$—, —OC(O)O—, —NR$^c$C(O)O—, —NR$^c$C(O)NR$^c$—, —OC(O)NR$^c$—, —C(=O)—, and —NR$^c$SO₂NR$^c$—;

each Z is independently selected from hydrogen, aryl, cycloalkyl, cycloalkenyl, heteroaryl and heterocyclic;

n is 0, 1 or 2; and x is 1 or 2;

or a pharmaceutically acceptable salt, stereoisomer, or prodrug thereof;

Preferably, R¹ is an amino containing saccharide group substituted on the amine with a group comprising two or more (e.g. 2, 3, 4, 5, or 6) hydroxy groups that is selected from —R$^a$—Y—R$^b$—(Z)$_x$, R$^f$, —C(O)R$^f$, and —C(O)—R$^a$—Y—R$^b$—(Z). For example, R¹ is preferably a saccharide group of the formula:

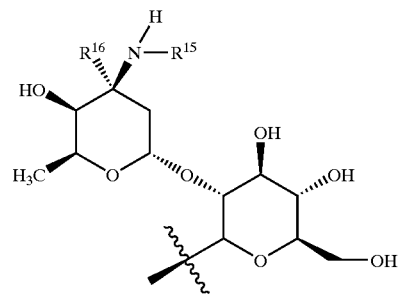

wherein R¹⁵ comprises two or more (e.g. 2, 3, 4, 5, or 6) hydroxy groups and is selected from —R$^a$—Y—R$^b$—(Z)$_x$, R$^f$, —C(O)R$^f$, and —C(O)—R$^a$—Y—R$^b$—(Z)$_x$; and R¹⁶ is hydrogen or methyl. In one preferred embodiment R¹⁵ is substituted alkyl, substituted alkenyl, substituted alkynyl, substituted cycloalkyl, substituted cycloalkenyl, aryl, heteroaryl, heterocyclic, substituted alkyl-C(O)—, substituted alkenyl-C(O)—, substituted alkynyl-C(O)—, substituted cycloalkyl-C(O)—, substituted cycloalkenyl-C(O)—, aryl-C(O)—, heteroaryl-C(O)—, or heterocyclic-C(O)—;

wherein $R^{15}$ comprises two or more hydroxy groups. More preferably, $R^{15}$ is substituted alkyl, substituted alkenyl, substituted alkynyl, substituted alkyl-C(O)—, substituted alkenyl-C(O)—, substituted alkynyl-C(O)—; wherein $R^{15}$ comprises two or more hydroxy groups.

In another preferred embodiment $R^{15}$ is a group of formula —$CH_2$—CH(OH)CH(OH)$CH_2$—Y—$R^b$—$(Z)_x$, or —$CH_2$—CH(OH)CH(OH)$CH_2$—$R^{17}$ wherein Y, $R^b$, Z and x have any of the values or preferred values described herein, and $R^{17}$ is hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic.

Preferably, $R^2$ is hydrogen.

Preferably, $R^3$ is —$OR^c$ or —$NR^cR^c$; more preferably $R^3$ is —OH.

Particularly preferred $R^3$ groups include —OH; —NH—$(CH_2)_3$—$N(CH_3)_2$N-(D—glucosamine); —NHCH($CO_2CH_3$)$CH_2CO_2CH_3$; —NH($CH_2)_3$-(morpholin-4-yl); —NH($CH_2)_3$—NH($CH_2)_2CH_3$; —NH($CH_2$-piperidin-1-yl; —NH($CH_2)_4$NHC(N)$NH_2$; —NH($CH_2)_2$-$N^+(CH_3)_3$; —NHCH(COOH)($CH_2)_3$NHC(N)$NH_2$; —NH—[($CH_2)_3$—NH—]$_3$—H; —N[($CH_2)_3N(CH_3)_2]_2$; —NH($CH_2)_3$-imidazol-1-yl; —$NHCH_2$-4-pyridyl; —NH($CH_2)_3CH_3$; —NH($CH_2)_2OH$; —NH($CH_2)_5OH$; —NH($CH_2)_2OCH_3$; —$NHCH_2$-tetrahydrofuran-2-yl; —N[($CH_2)_2OH]_2$; —NH($CH_2)_2N[(CH_2)_2OH]_2$; —$NHCH_2COOH$; —NHCH(COOH)$CH_2OH$; —NH($CH_2)_2COOH$; N-(glucamine); —NH($CH_2)_2COOH$; —NH($CH_2)_3SO_3H$; —NHCH(COOH)($CH_2)_2NH_2$; —NHCH(COOH)($CH_2)_3NH_2$; —NHCH(COOH)$CH_2CO_2(CH_2)_3$-$N^+(CH_3)_3$; —NHCH(COOH)$CH_2CO_2(CH_2)_2C(O)$—$N(CH_3)_2$; —NHCH(COOH)$CH_2CO_2(CH_2)_3$-morpholin-4-yl; —NHCH(COOH)$CH_2CO_2(CH_2)_2OC(O)C(CH_3)_3$; —NHCH($CH_2COOH$)$CO_2(CH_2)_3$—$N^+(CH_3)_3$; —NHCH($CH_2COOH$)$CO_2(CH_2)_2C(O)N(CH_3)_2$; —NHCH($CH_2COOH$)$CO_2(CH_2)_3$-morpholin-4-yl; —NHCH($CH_2COOH$)$CO_2(CH_2)_2OC(O)C(CH_3)_3$, —NHCH(COOH)$CH_2CO_2CH_3$; —NHCH($CH_2COOH$)$CO_2(CH_2)_2N(CH_3)_2$; —NHCH(COOH)$CH_2CO_2CH_2C(O)N(CH_3)_2$; —NHCH($CH_2COOH$)$CO_2CH_2C(O)N(CH_3)_2$; —NHCH($CH_2COOH$)$CO_2CH_3$; —NH($CH_2)_3N(CH_3)_2$; —$NHCH_2CH_2CO_2CH_3$; —NHCH[$CH_2CO_2CH_2C(O)N(CH_3)_2$]—$CO_2CH_2$—C(O)—$N(CH_3)_2$; —$NHCH_2CO_2CH_3$; -N-(methyl 3-amino-3-deoxyaminopyranoside); -N-(methyl 3-amino-2,3,6-trideoxyhexopyranoside); —N-(2-amino-2-deoxy-6-(dihydrogenphosphate)-glucopyranose; -N-(2-amino-2-deoxygluconic acid); —NH($CH_2)_4COOH$; —N—(N—$CH_3$-D-glucamine; —NH($CH_2)_6COOH$; —O(D-glucose); —NH($CH_2)_3OC(O)CH(NH_2)CH_3$; —NH($CH_2)_4CH(C(O)-2-HOOC-pyrrolidin-1-yl)NHCH(COOH)$-$CH_2CH_2Ph$ (S,S isomer); —NH—$CH_2CH_2$—NH—($CH_2)_9CH_3$; —NH($CH_2)C(O)CH_2C(O)N(CH_3)_2$;

Preferably, $R^4$, $R^6$ and $R^7$ are each independently selected from hydrogen or —$C(O)R^d$. More preferably, $R^4$, $R^6$ and $R^7$ are each hydrogen.

Preferably $R^5$ is hydrogen, —$CH_2$—$NHR^c$, —$CH_2$—$NR^cR^e$ or —$CH_2$—NH—$R^a$—Y—$R^b$—$(Z)_x$. $R^5$ can also preferably be hydrogen; —$CH_2$—N—(N—$CH_3$-D-glucamine); —$CH_2$—NH—$CH_2CH_2$—NH—($CH_2)_9CH_3$; —$CH_2$—NH—$CH_2CH_2$—NHC(O)—($CH_2)_3COOH$; —$CH_2$—NH—($CH_2)_9CH_3$;-$CH_2$—NH—$CH_2CH_2$—COOH; —$CH_2$—NH—($CH_2)_5COOH$; —$CH_2$-(morpholin-4-yl); —$CH_2$—NH—$CH_2CH_2$—O—$CH_2CH_2OH$; —$CH_2$—NH—$CH_2CH(OH)$—$CH_2OH$; —$CH_2$—N[$CH_2CH_2O$ H]$_2$; —$CH_2$—NH—($CH_2)_3$—$N(CH_3)_2$; —$CH_2$—N[($CH_2)_3$—$N(CH_3)_2]_2$; —$CH_2$—NH—($CH_2)_3$-(imidazol-1-yl); —$CH_2$—NH—($CH_2)_3$-(morpholin-4-yl); —$CH_2$—NH—($CH_2)_4$—NHC(NH)$NH_2$; —$CH_2$-N-(2-amino-2-deoxygluconic acid);—$CH_2$—NH—$CH_2CH_2$—NH—($CH_2)_{11}CH_3$; —$CH_2$—NH—CH(COOH)$CH_2COOH$; —$CH_2$—NH—$CH_2CH_2$—$NHSO_2$—($CH_2)_7CH_3$; —$CH_2$—NH—$CH_2CH_2$—$NHSO_2$—($CH_2)_8CH_3$; —$CH_2$—NH—$CH_2CH_2$—$NHSO_2$—($CH_2)_9CH_3$; —$CH_2$—NH—$CH_2CH_2$—$NHSO_2$—($CH_2)_{11}CH_3$; —$CH_2$—NH—$CH_2CH_2$—NH—($CH_2)_7CH_3$; —$CH_2$—NH—$CH_2CH_2$—O—$CH_2$ $CH_2OH$; —$CH_2$—NH—$CH_2CH_2C(O)$—N-(D-glucosamine); —$CH_2$—NH—(6-oxo-[1,3]oxazinan-3-yl); —$CH_2$—NH—$CH_2CH_2$—S——$CH_2$—NH—$CH_2CH_2$—S—($CH_2)_8CH_3$; —$CH_2$—NH—$CH_2CH_2$—S—($CH_2)_9CH_3$; —$CH_2$—NH—$CH_2CH_2$—S—($CH_2)_{11}CH_3$; —$CH_2$—NH—$CH_2CH_2$—S—($CH_2)_6Ph$; —$CH_2$—NH—$CH_2CH_2$—S—($CH_2)_8Ph$; —$CH_2$—NH—$CH_2CH_2$—S—($CH_2)_{10}Ph$; —$CH_2$—NH—$CH_2CH_2$—S—$CH_2$-(4-(4—$CF_3$—Ph)Ph); —$CH_2$—NH—$CH_2CH_2$—NH—($CH_2)_{11}CH_3$; or —$CH_2$—NH—($CH_2)_5$—COOH.

Preferably, $R^8$ is —$CH_2C(O)NH_2$, —$CH_2COOH$, benzyl, 4-hydroxyphenyl or 3-chloro-4-hydroxyphenyl.

Preferably, $R^9$ is hydrogen or alkyl.

Preferably, $R^{10}$ is alkyl or substituted alkyl. More preferably, $R^{10}$ is the side-chain of a naturally occurring amino acid, such as isobutyl.

Preferably, $R^{11}$ is hydrogen or alkyl.

Preferably, $R^{12}$ is hydrogen, alkyl, substituted alkyl or —$C(O)R^d$. $R^{12}$ can also preferably be hydrogen; —$CH_2COOH$; —$CH_2$—[CH(OH)]$_5$CH2OH; —$CH_2CH(OH)CH_2OH$; —$CH_2CH_2NH_2$; —$CH_2C(O)OCH_2CH_3$; —$CH_2$-(2-pyridyl); —$CH_2$—[CH(OH)]$_4$COOH; —$CH_2$-(3-carboxyphenyl); (R)—C(O)CH($NH_2$)($CH_2)_4NH_2$; —C(O)Ph; —C(O)$CH_2$NHC(O)$CH_3$; E—$CH_2CH_2$—S—($CH_2)_3$CH=CH($CH_2)_4CH_3$; or —C(O)$CH_3$.

Preferably, $X^1$ and $X^2$ are each chloro.

Preferably, $X^3$ is hydrogen.

Preferably, each Y is independently selected from the group consisting of oxygen, sulfur, —S—S—, —$NR^c$—, —S(O)—, —$SO_2$—, —$NR^cC(O)$—, —$OSO_2$—, —OC(O)—, —$NR^cSO_2$—, —C(O)$NR^c$—, —C(O)O—, —$SO_2NR^c$—, —$SO_2O$—, —P(O)($OR^c$)O—, —P(O)($OR^c$)$NR^c$—, —OP(O)($OR^c$)O—,—OP(O)($OR^c$)$NR^c$—, —OC(O)O—, —$NR^cC(O)O$—, —$NR^cC(O)NR^c$—, —OC(O)$NR^c$—, and —$NR^cSO_2NR^c$–;

Preferably, n is 0 or 1, and more preferably, n is 1.

Preferred compounds of the invention exclude glycopeptide derivatives substituted at the C-terminus with a substituent that comprises more than one carboxy (COOH) group.

Preferred compounds of the invention exclude glycopeptide derivatives substituted at the C-terminus with a substituent that comprises one or more saccharide groups and a carboxy (COOH) group.

Certain glycopeptide derivatives are described in U.S. patent application Ser. No. 09/470,209, filed Dec. 22, 1999. Accordingly, the compounds of the invention may preferably exclude glycopeptides of formula II:

(II)
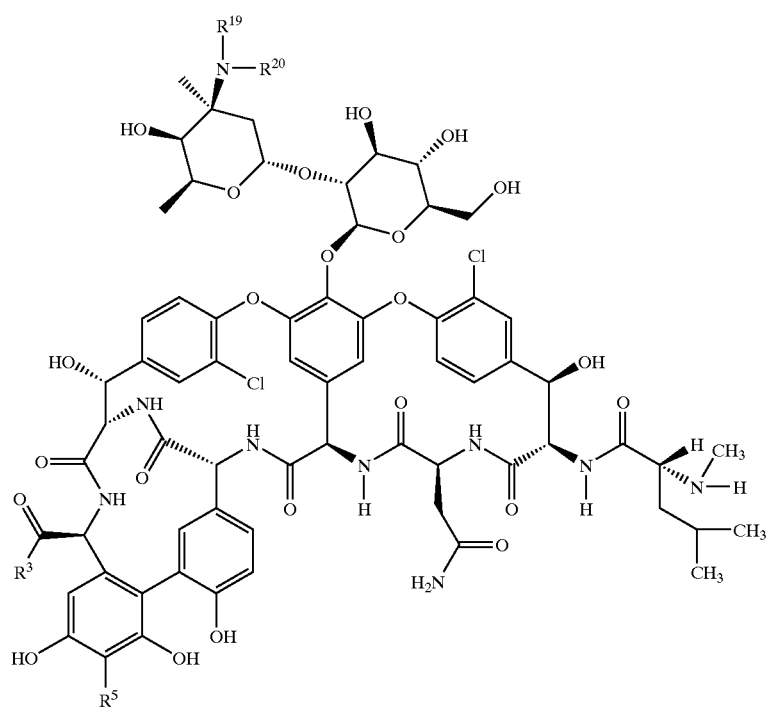
a) wherein $R^3$ is OH; $R^5$ is hydrogen; $R^{19}$ is —CH$_2$[CH(OH)]$_4$COOH; and $R^{20}$ is —CH$_2$CH$_2$—NH—(CH$_2$)$_9$CH$_3$; or
b) wherein $R^3$ is OH; $R^5$ is hydrogen; $R^{19}$ is hydrogen; and $R^{20}$ is —CH$_2$CH$_2$—N(C(O)-3,4,5-trihydroxycyclohex-1-en-1-yl)-(CH$_2$)$_9$CH$_3$ (R,S,R isomer);
A preferred compound of the invention is a glycopeptide of formula II:
(II)
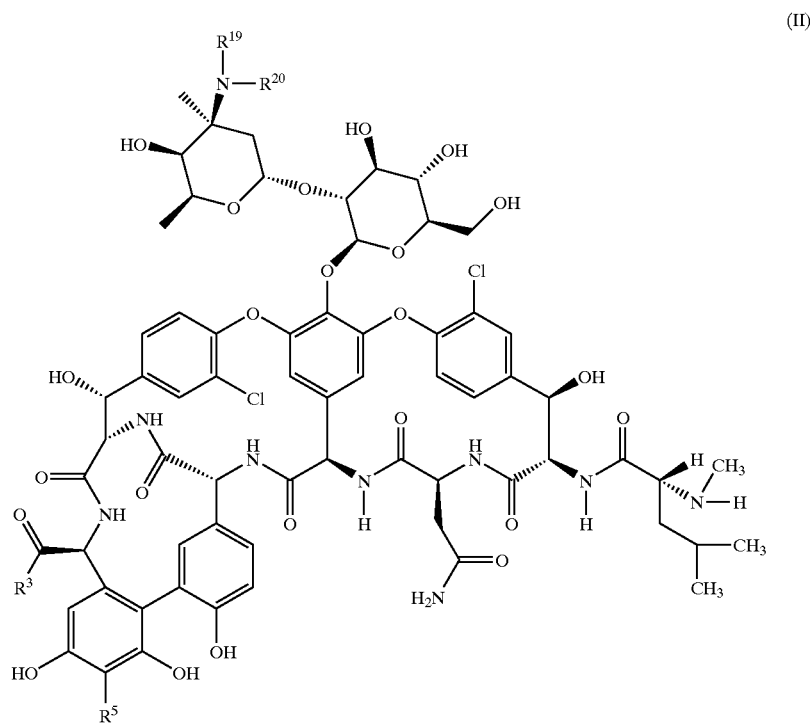

wherein:

$R^{19}$ is hydrogen;

$R^{20}$ comprises two or more (e.g. 2, 3, 4, 5, or 6) hydroxy groups and is selected from $-R^a-Y-R^b-(Z)_x$, $R^f$, $-C(O)R^f$, and $-C(O)-R^a-Y-R^b-(Z)_x$; and $R^a$, Y, $R^b$, Z, x, $R^f$, $R^3$, and $R^5$ have any of the values or preferred values described herein;

or a pharmaceutically acceptable salt, stereoisomer, or prodrug thereof, provided the group $R^3$ does not comprise more than one carboxy group; and provided the group $R^3$ is not a substituent that comprises one or more saccharide groups and a carboxy (COOH) group.

In one preferred embodiment $R^{20}$ is substituted alkyl, substituted alkenyl, substituted alkynyl, substituted cycloalkyl, substituted cycloalkenyl, aryl, heteroaryl, heterocyclic, substituted alkyl-C(O)—, substituted alkenyl-C(O)—, substituted alkynyl-C(O)—, substituted cycloalkyl-C(O)—, substituted cycloalkenyl-C(O)—, aryl-C(O)—, heteroaryl-C(O)—, or heterocyclic-C(O)—; wherein $R^{15}$ comprises two or more hydroxy groups. More preferably, $R^{20}$ is substituted alkyl, substituted alkenyl, substituted alkynyl, substituted alkyl-C(O)—, substituted alkenyl-C(O)—, substituted alkynyl-C(O)—; wherein $R^{20}$ comprises two or more hydroxy groups.

In another preferred embodiment $R^{20}$ is a group of formula $-CH_2-CH(OH)CH(OH)CH_2-Y-R^b-(Z)_x$, or $-CH_2-CH(OH)CH(OH)CH_2-R^{17}$ wherein Y, $R^b$, Z and x have any of the values or preferred values described herein, and $R^{17}$ is hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic.

The invention also provides a pharmaceutical composition comprising a pharmaceutically acceptable carrier and a therapeutically effective amount of a compound of the invention. In one preferred embodiment, the pharmaceutically acceptable carrier comprises an aqueous cyclodextrin solution. Preferably, the cyclodextrin is hydroxypropyl-β-cyclodextrin or sulfobutyl ether β-cyclodextrin. More preferably, the cyclodextrin is hydroxypropyl-β-cyclodextrin.

The compounds of the invention are highly effective antibacterial agents. Accordingly, the invention also provides a method of treating a mammal having a bacterial disease, comprising administering to the mammal a therapeutically effective amount of a compound of the invention. The invention also provides a method of treating a mammal having a bacterial disease, comprising administering to the mammal a therapeutically effective amount of a pharmaceutical composition of the invention.

The invention also provides processes and intermediates useful for preparing compounds of the invention, which processes and intermediates are described further herein.

The invention also provides a compound of the invention as described herein for use in medical therapy, as well as the use of a compound of the invention in the manufacture of a formulation or medicament for treating a bacterial disease in a mammal.

Preferred compounds of the invention are the compounds of formula II shown in Table I below wherein $R^{19}$ is hydrogen.

TABLE I

Preferred Compounds of formula II

| Compound | $R^3$ | $R^5$ | $R^{20}$ |
|---|---|---|---|
| 1 | OH | H | $-CH_2-CH(OH)-CH(OH)-(CH_2)_9CH_3$ |
| 2 | OH | H | $-CH_2-CH(OH)-CH(OH)-(CH_2)_{11}CH_3$ |
| 3 | OH | H | $-CH_2-CH(OH)-CH(OH)-CH_2S(CH_2)_9CH_3$ |
| 4 | OH | H | $-CH_2-CH(OH)-CH(OH)-(4'\text{-chlorobiphenyl})$ |

Another preferred group of compounds of the invention are polyhydroxy derivatives of the glycopeptide antibiotic A82846B (also known as chloroorienticin A oy LY264826). See for example R. Nagarajan et al., *J Org Chem.*, 1988, 54, 983–986; and N. Tsuji et al., *J. Antibiot.*, 1988, 41, 819–822. The structure of this glycopeptide is similar to vancomycin, except A82846B contains an additional amino sugar (i.e. 4-epi-vancosamine attached at the $R^2$ position in formula I.) and further contains 4-epi-vancosamine in place of vancosamine in the disaccharide moiety attached at the $R^1$ position in formula I. For example, a preferred group of compounds are derivatives of A82846B that are substituted at the 4-epi-vancosamine nitrogen with a substituent that comprises two or more (e.g. 2, 3, 4, 5, or 6) hydroxy groups; or a pharmaceutically acceptable salt, stereoisomer, or prodrug thereof. Another preferred group of compounds of the invention are derivatives of A82846B wherein the 4-epi-vancosamine has been replaced with a group selected from the values defined herein for $R^1$ in a compound of formula I. The compounds of the invention that are polyhydroxy derivatives of A82846B can readily be prepared using the procedures described herein.

The polyhydroxy glycopeptide derivatives of the invention have been found to unexpectedly exhibit reduced tissue accumulation and/or nephrotoxicity when administered to a mammal. While not wishing to be bound by theory, it is believed that the hydroxy groups serve to increase the overall polarity of the glycopeptide under physiological conditions thereby facilitating excretion from the mammal after administration. The unexpected increase in excretion of the polyhydroxy compounds of the invention may be responsible for the reduced tissue accumulation and/or reduced nephrotoxicity observed for these compounds relative to the corresponding compounds that lack the hydroxy groups functionality.

DETAILED DESCRIPTION OF THE INVENTION

This invention relates to novel compounds of the invention, which are polyhydroxy derivatives of glycopeptide antibiotics, as well as to compositions comprising such compounds and to therapeutic methods comprising the administration of such compounds. When describing the compounds, compositions and methods of the invention, the following terms have the following meanings, unless otherwise indicated.

Definitions

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 8 substituents, preferably 1 to 5 substituents, and more preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, guanido, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, SO$_3$H, and —SO2-heteroaryl.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of aikoxy, substituted alkoxy, cycloalkyl, substituted cycloalkyl, cycloalkenyl, substituted cycloalkenyl, acyl, acylamino, acyloxy, amino, substituted amino, aininoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —S$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures. Additionally, the term substituted alkylene includes alkylene groups m which from 1 to 5 of the alkylene carbon atoms are replaced with oxygen, sulfur or —NR—where R is hydrogen or alkyl. Examples of substituted alkylenes arc chloromethylene (—CH(CI)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$ O—CH$_2$CH$_2$—) and the like.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH═CH$_2$), n-propenyl (—CH$_2$CH═CH$_2$), iso-propenyl (—C(CH$_3$)═CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH═CH—), the propenylene isomers (e.g., —CH$_2$CH═CH— and —C(CH$_3$)═CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO2-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group -C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, sulfonamide, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

The term "carboxy" refers to —COOH.

The term "C-terminus" as it relates to a glycopeptide is well understood in the art. For example, for a glycopeptide of formula I, the C-terminus is the position substituted by the group $R^3$.

The term "dicarboxy-substituted alkyl" refers to an alkyl group substituted with two carboxy groups. This term includes, by way of example, —$CH_2$(COOH)$CH_2$COOH and —$CH_2$(COOH)$CH_2CH_2$COOH.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "halo" or "halogen" refers to fluoro, chloro, bromo or iodo.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroarylalkyl" refers to (heteroaryl)alkyl- where heteroaryl and alkyl are as defined herein. Representative examples include 2-pyridylmethyl and the like.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benozofuranylene, 2,5-pyridnylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, oxo (═O), and —$SO_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula [—(CH$_2$—)$_a$A-] where a is equal to or greater than 2, and A at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "phosphono" refers to —PO$_3$H$_2$.

The term "prodrug" is well understood in the art and includes compounds that are converted to pharmaceutically active compounds of the invention in a mammalian system. For example, see Remington's Pharmaceutical Sciences, 1980, vol. 16, Mack Publishing Company, Easton, Pa., 61 and 424.

The term "saccharide group" refers to an oxidized, reduced or substituted saccharide monoradical covalently attached to the glycopeptide or other compound via any atom of the saccharide moiety, preferably via the aglycone carbon atom. The term includes amino-containing saccharide groups. Representative saccharides include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, -methyl-D-glucamine, D-glucuronic acid, N-acetyl-D-glucosamine, -acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, these saccharides are referenced using conventional three letter nomenclature and the saccharides can be either in their open or preferably in their pyranose form.

The term "amino-containing saccharide group" or "amino saccharide" refers to a saccharide group having an amino substituent. Representative amino-containing saccharides include L-vancosamine, 3-desmethyl-vancosamine, 3-epi-vancosamine, 4-epi-vancosamine, acosamine, actinosamine, daunosamine, 3-epi-daunosamine, ristosamine, -methyl-D-glucamine and the like.

The term "spiro-attached cycloalkyl group" refers to a cycloalkyl group attached to another ring via one carbon atom common to both rings.

The term "stereoisomer" as it relates to a given compound is well understood in the art, and refers another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, Morrison and Boyde Organic Chemistry, 1983, 4th ed., Allyn and Bacon, Inc., Boston, Mass., page 123

The term "sulfonamide" refers to a group of the formula —SO$_2$NRR, where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "thioether derivatives" when used to refer to the glycopeptide compounds of this invention includes thioethers (—S—), sulfoxides (—SO—) and sulfones (—SO$_2$—).

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Cyclodextrin" refers to cyclic molecules containing six or more α-D-glucopyranose units linked at the 1,4 positions by α linkages as in amylose. β-Cyclodextrin or cycloheptaamylose contains seven α-D-glucopyranose units. As used herein, the term "cyclodextrin" also includes cyclodextrin derivatives such as hydroxypropyl and sulfobutyl ether cyclodextrins. Such derivatives are described for example, in U.S. Pat. Nos. 4,727,064 and 5,376,645. One preferred cyclodextrin is hydroxypropyl β-cyclodextrin having a degree of substitution of from about 4.1–5.1 as measured by FTIR. Such a cyclodextrin is available from Cerestar (Hammond, Ind., USA) under the name CavitronTm 82003.

"Glycopeptide" refers to oligopeptide (e.g. heptapeptide) antibiotics characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences"Volume 63, edited by Ramakrishnan Nagaraj an, published by Marcal Dekker, Inc.). Additional examples of glycopeptides are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107–13108; J. Amer. Chem. Soc., 1997, 119, 12041–12047; and J. Amer. Chem. Soc., 1994, 116, 4573–4590. Representative glycopeptides include those identified as A477, A35512, A40926, A41030, A42867, A47934, A80407, A82846, A83850 ,A84575, AB-65, Actaplanin, Actinoidin, Ardacin, Avoparcin, Azureomycin, Balhimycin, Chloroorientiein, Chloropolysporin, Decaplanin, N-demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, Vancomycin, and the like. The term "glycopeptide" as used herein is also intended to include the general class of peptides disclosed above on which the sugar moiety is absent, i.e. the aglycone series of glycopeptides. For example, removal of the disaccharide moiety appended to the phenol on vancomycin by mild hydrolysis gives vancomycin aglycone. Also within the scope of the invention are glycopeptides that have been further appended with additional saccharide residues, especially aminoglycosides, in a manner similar to vancosamine.

"Vancomycin" refers to a glycopeptide antibiotic having the formula:

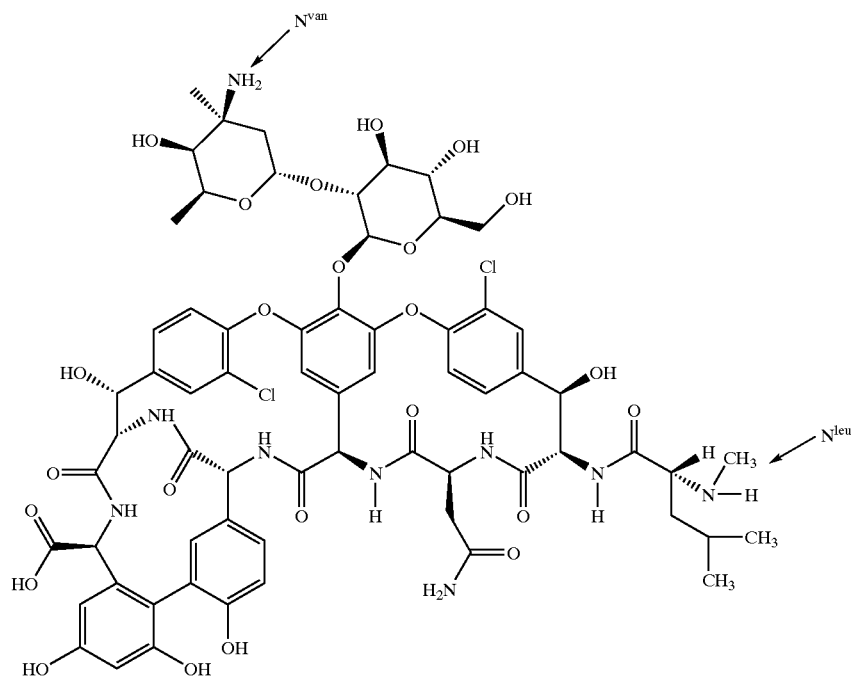

When describing vancomycin derivatives, the term "$N^{van}$-" indicates that a substituent is covalently attached to the amino group of the vacosamine moiety of vacomycin. Similarly, the term "$N^{leu}$-" indicates that a substituent is covalently attached to the amino group of the leucine moiety of vancomycin.

"Optional" or "optionally" means that the subsequently described event or circumstance may or may not occur, and that the description includes instances where said event or circumstance occurs and instances in which it does not. For example, "optionally substituted" means that a group may or may not be substituted with the described substituent.

As used herein, the terms "inert organic solvent" or "inert solvent" or "inert diluent" mean a solvent or diluent which is essentially inert under the conditions of the reaction in which it is employed as a solvent or diluent. Representative examples of materials which may be used as inert solvents or diluents include, by way of illustration, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The term "nitrogen-linked" means a group or substituent is attached to the remainder of a compound (e.g. a compound of formula I) through a bond to a nitrogen of the group or substituent.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of this invention typically contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The term "treatment" as used herein includes any treatment of a condition or disease in an animal, particularly a mamimal, more particularly a human, and includes:

(i) preventing the disease or condition from occurring in a subject which may be predisposed to the disease but has not yet been diagnosed as having it;

(ii) inhibiting the disease or condition, i.e. arresting its development; relieving the disease or condition, i.e. causing regression of the condition; or. relieving the conditions caused by the disease, i.e. symptoms of the disease.

The term "disease state which is alleviated by treatment with a broad spectrum antibacterial" or "bacterial disease" as used herein is intended to cover all disease states which are generally acknowledged in the art to be usefully treated with a broad spectrum antibacterial in general, and those disease states which have been found to be usefully treated by the specific antibacterials of this invention. Such disease states include, but are not limited to, treatment of a mammal afflicted with pathogenic bacteria, in particular staphylococci (methicillin sensitive and resistant), streptococci (penicillin sensitive and resistant), enterococci (vancomycin sensitive and resistant), and Clostridium difficile The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

The term "protecting group" or "blocking group" refers to any group which, when bound to one or more hydroxyl, thiol, amino, carboxy or other groups of the compounds, prevents undesired reactions from occurring at these groups and which protecting group can be removed by conventional chemical or enzymatic steps to reestablish the hydroxyl, thio, amino, carboxy or other group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" 3rd Ed., 1999, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxy protecting groups include esters such as methyl, ethyl, propyl, t-butyl etc. which can be removed by mild conditions compatible with the nature of the product.

General Synthetic Procedures

The glycopeptide compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis,* Third Edition, Wiley, N.Y., 1999, and references cited therein.

In the following reaction schemes, the glycopeptide compounds are depicted in a simplified form as a box "G" that shows the carboxy terminus labeled [C], the vancosamine amino terminus labeled [V], the "non-saccharide" amino terminus (leucine amine moiety) labeled [N], and optionally, the resorcinol moiety labeled [R] as follows:

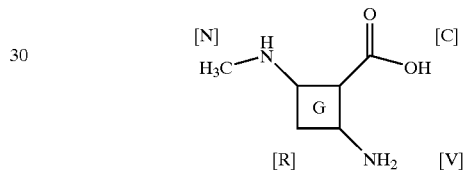

By way of illustration, a glycopeptide compound, such as vancomycin, can be reductively alkylated as shown in the following reaction:

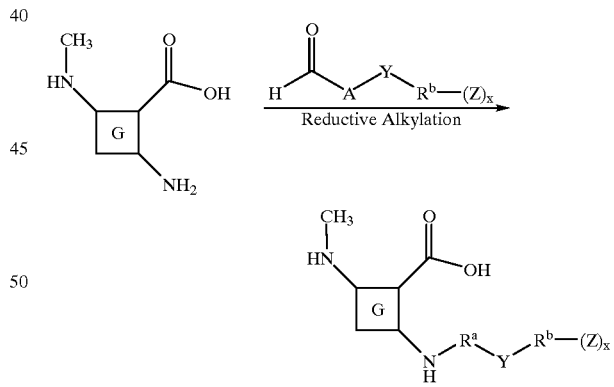

where A represents $R^a$ minus one carbon atom and $R^a$, $R^b$, Y, Z and x are as defined herein. This reaction is typically conducted by first contacting one equivalent of the glycopeptide, i.e., vancomycin, with an excess, preferably from 1.1 to 1.3 equivalents, of the desired aldehyde in the presence of an excess, preferably about 2.0 equivalents, of a tertiary amine, such as diisopropylethylamine (DIPEA) and the like. This reaction is typically conducted in an inert diluent, such as DMF or acetonitrile/water, at ambient temperature for about 0.25 to 2 hours until formation of the corresponding imine and/or hemiaminal is substantially complete. The resulting imine and/or hemiaminal is typically not isolated, but is reacted in situ with a metal hydride reducing agent, such as sodium cyanoborohydride or the like, to afford the corresponding amine. This reaction is preferably conducted by contacting the imine and/or hemiaminal with an excess, preferably about 3 equivalents, of trifluoroacetic acid, followed by about 1 to 1.2 equivalents of the reducing agent at ambient temperature in methanol or acetonitrile/water. The resulting alkylated product is readily purified by conventional procedures, such as precipitation and/or reverse-phase HPLC. Surprisingly, by forming the imine and/or hemiaminal in the presence of a trialkyl amine, and then acidifying with trifluoroacetic acid before contact with the reducing agent, the selectivity for the reductive alkylation reaction is greatly improved, i.e., reductive alkylation at the amino group of the saccharide (e.g., vancosamine) is favored over reductive alkylation at the N-terminus (e.g., the leucinyl group) by at least 10:1, more preferably 20:1.

The above process is a significantly improvement over previous methods for selectively alkylating an amino saccharide group of a glycopeptide antibiotic. Thus, the present invention also provides a method for alkylating a glycopeptide that comprises a saccharide-amine comprising:

combining an aldehyde or ketone, a suitable base, and the glycopeptide, to provide a reaction mixture;

acidifying the reaction mixture; and combining the reaction mixture with a suitable reducing agent, to provide a glycopeptide that is alkylated at the saccharide-amine. Preferably, the glycopeptide comprises at least one amino group other than the saccharide-amine.

Preferably, the reductive alkylation at the saccharide-amine is favored over reductive alkylation at another amino group of the glycopeptide by at least about 10:1; and more preferably, by at least about 15:1 or about 20:1.

The reductive alkylation process of the invention is typically carried out in the presence of a suitable solvent or combination of solvents, such as, for example, a halogenated hydrocarbon (e.g. methylene chloride), a linear or branched ether (e.g. diethyl ether, tetrahydrofuran), an aromatic hydrocarbon (e.g. benzene or toluene), an alcohol (methanol, ethanol, or isopropanol), dimethylsulfoxide (DMSO), N,N-dimethylformamide, acetonitrile, water, 1,3-dimethyl-3,4,5,6-tetrahydro-2(1H)-pyrimidone, tetramethyl urea, N,N-dimethylacetamide, diethylformamide (DMF), 1-methyl-2-pyrrolidinone, tetramethylenesulfoxide, glycerol, ethyl acetate, isopropyl acetate, N,N-dimethylpropylene urea (DMPU) or dioxane. Preferably the alkylation is carried out in acetonitrile/water, or DMF/methanol.

Preferably the reduction (i.e. treatment with the reducing agent) is carried out in the presence of a protic solvent, such as, for example, an alcohol (e.g. methanol, ethanol, propanol, isopropanol, or butanol), water, or the like.

The reductive alkylation process of the invention can be carried out at any suitable temperature from the freezing point to the reflux temperature of the reaction mixture. Preferably the reaction is carried out at a temperature in the range of about 0° C. to about 100° C. More preferably at a temperature in a range of about 0° C. to about 50° C., or in a range of about 20° C. to about 30° C.

Any suitable base can be employed in the reductive alkylation process of the invention. Suitable bases include tertiary amines (e.g. diisopropylethylamine, N-methylmorpholine or triethylamine) and the like.

Any suitable acid can be used to acidify the reaction mixture. Suitable acids include carboxylic acids (e.g. acetic acid, trichloroacetic acid, citric acid, formic acid, or trifluoroacetic acid), mineral acids (e.g. hydrochloric acid, sulfuric acid, or phosphoric acid), and the like. A preferred acid is trifluoroacetic acid.

Suitable reducing agents for carrying out reductive alkylation process of the invention are known in the art. Any suitable reducing agent can be employed in the methods of the invention, provided it is compatible with the flnctionality present in the glycopeptide. For example, suitable reducing agents include sodium cyanoborohydride, triacetoxyborohydride, pyridine/borane, sodium borohydride, and zinc borohydride. The reduction can also be carried out in the presence of a transition metal catalyst (e.g. palladium or platinum) in the presence of a hydrogen source (e.g. hydrogen gas or cycloheadiene). See for example, , Advanced Organic Chemistry, Fourth Edition, John Wiley & Sons, New York (1992), 899–900.

If desired, the glycopeptide compounds of this invention can also be prepared in a step-wise manner in which a precursor to the —R$^a$—Y—R$^b$—(Z)$_x$ group is first attached the glycopeptide by reductive alkylation, followed by subsequent elaboration of the attached precursor using conventional reagent and procedures to form the —R$^a$—Y—R$^b$—(Z)$_x$ group. Additionally, ketones may also be employed in the above-described reductive alkylation reactions to afford a-substituted amines.

Any glycopeptide having an amino group may be employed in these reductive alkylation reactions. Such glycopeptides are well-known in the art and are either commercially available or may be isolated using conventional procedures. Suitable glycopeptides are disclosed, by way of example, in U.S. Pat. Nos. 3,067,099; 3,338,786; 3,803,306; 3,928,571; 3,952,095; 4,029,769; 4,051,237; 4,064,233; 4,122,168; 4,239,751; 4,303,646; 4,322,343; 4,378,348; 4,497,802; 4,504,467; 4,542,018; 4,547,488; 4,548,925; 4,548,974; 4,552,701; 4,558,008; 4,639,433; 4,643,987; 4,661,470; 4,694,069; 4,698,327; 4,782,042; 4,914,187; 4,935,238; 4,946,941; 4,994,555; 4,996,148; 5,187,082; 5,192,742; 5,312,738; 5,451,570; 5,591,714; 5,721,208; 5,750,509; 5,840,684; and 5,843,889. Preferably, the glycopeptide employed in the above reaction is vancomycin.

As illustrated in the following scheme, an aminoalkyl sidechain at the resorcinol moiety of a glycopeptide, such as vancomycin, can be introduced via a Mannich reaction (in this scheme, the resorcinol moiety is shown for clarity). In this reaction, an amine (NHRCRC) and an aldehyde (CH$_2$O), such as formalin (a source of formaldehyde), are reacted with the glycopeptide under basic conditions to give the glycopeptide derivative.

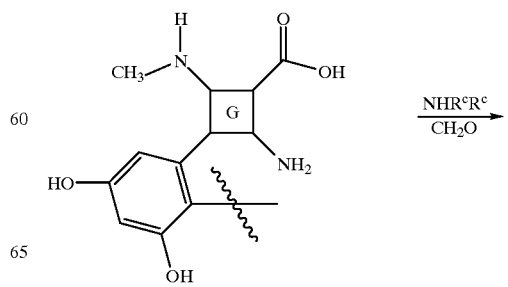

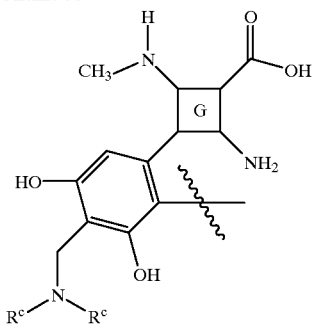

Compounds of the invention comprising a sulfoxide or sulfone can be prepared from the corresponding thio compounds using conventional reagents and procedures. Suitable reagents for oxidizing a thio compound to a sulfoxide include, by way of example, hydrogen peroxide, peracides such as 3-chloroperoxybenzoic acid (MCPBA), sodium periodate, sodium chlorite, sodium hypochlorite, calcium hypochlorite, tert-butyl hypochlorite and the like. Chiral oxidizing reagents, (optically active reagents) may also be employed to provide chiral sulfoxides. Such optically active reagents are well-known in the art and include, for example, the reagents described in Kagen et al., *Synlett.*, 1990, 643–650.

The aldehydes and ketones employed in the above reactive alkylation reactions are also well-known in the art and are either commercially available or can be prepared by conventional procedures using commercially available starting materials and conventional reagents (for example see March, *Advanced Organic Chemistry*, Fourth Edition, John Wiley & Sons, New York (1992), and references cited therein).

The polyhydroxy aldehydes are commercially available, can be prepared by conventional procedures using commercially available starting materials and reagents, or can be prepared as illustrated below. Hydroxylation of an olefin 1 provides a diol of formula 2, which can be protected with a suitable protecting group "Pg" (e.g. as the bis(TMS-ether) to provide a compound of formula 3. Reduction of compound 3 with a suitable reducing agent (for example with DIBAL-H) provides an aldehyde of formula 4, which can be used to prepare compounds of the invention.

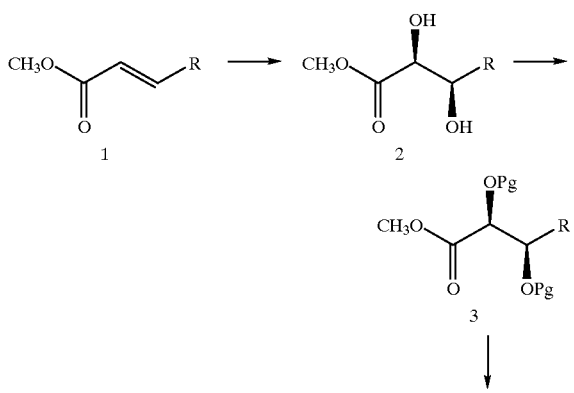

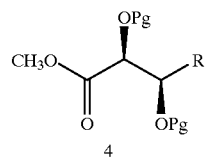

Additional details and other methods for preparing the compounds of this invention are described in the Examples below.

Pharmaceutical Compositions

This invention also includes pharmaceutical composition containing the novel glycopeptide compounds of this invention. Accordingly, the glycopeptide compound, preferably in the form of a pharmaceutically acceptable salt, can be formulated for oral or parenteral administration for the therapeutic or prophylactic treatment of bacterial infections.

By way of illustration, the glycopeptide compound can be admixed with conventional pharmaceutical carriers and excipients and used in the form of tablets, capsules, elixirs, suspensions, syrups, wafers, and the like. Such pharmaceutical compositions will contain from about 0. 1 to about 90% by weight of the active compound, and more generally from about 10 to about 30%. The pharmaceutical compositions may contain common carriers and excipients, such as corn starch or gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intra-muscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

In a preferred embodiment, the glycopeptide derivatives of this invention are formulated in an aqueous solution containing a cyclodextrin. In another preferred embodiment the glycopeptide derivatives of this invention are formulated as a lyophilized powder containing a cyclodextrin or as a sterile powder containing a cyclodextrin. Preferably, the cyclodextrin is hydroxypropyl-β-cyclodextrin or sulfobutyl ether β-cyclodextrin; more preferably, the cyclodextrin is hydroxypropyl-β-cyclodextrin. Typically, in an injectable solution, the cyclodextrin will comprise about 1 to 25 weight percent; preferably, about 2 to 10 weight percent; more preferable, about 4 to 6 weight percent, of the formulation. Additionally, the weight ratio of the cyclodextrin to the glycopeptide derivative will preferably be from about 1:1 to about 10:1.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or pulsatile infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991. Such patches may be constructed for continuous, pulsatile, or on demand delivery of pharmaceutical agents.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patients symptoms, and the like.

Suitable doses are in the general range of from 0.01–100 mg/kg/day, preferably 0.1–50 mg/kg/day. For an average 70 kg human, this would amount to 0.7 mg to 7 g per day, or preferably 7 mg to 3.5 g per day. A more preferred dose for a human is about 500 mg to about 2 g per day.

Other suitable formulations for use in the present invention can be found in *Remington's Pharmaceutical Sciences,* Mace Publishing Company, Philadelphia, Pa., 17th ed. (1985).

The following formulation examples illustrate representative pharmaceutical compositions of the present invention.

FORMULATION EXAMPLE A

This example illustrates the preparation of a representative pharmaceutical composition for oral administration of a compound of this invention:

| Ingredients | Quantity per tablet, (mg) |
| --- | --- |
| Active Compound | 200 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
| --- | --- |
| Active Compound | 400 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
| --- | --- |
| Active Compound | 1.0 g |
| Fumaric acid | 0.5 g |

-continued

| Ingredients | |
|---|---|
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
|---|---|
| Active Compound | 0.2 g |
| Sodium Acetate Buffer Solution (0.4 M) | 2.0 mL |
| HCl (1N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 g of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection

FORMULATION EXAMPLE F

This example illustrates the preparation of a representative pharmaceutical composition containing a compound of this invention.

An injectable preparation is prepared having the following composition:

| Ingredients | |
|---|---|
| Active Compound | 0.1–5.0 g |
| Hydroxypropyl-β-cyclodextrin | 1–25 g |
| 5% Aqueous Dextrose Solution (sterile) | q.s. to 100 mL |

The above ingredients are blended and the pH is adjusted to 3.5 ± 0.5 using 0.5 N HCl or 0.5 N NaOH.

FORMULATION EXAMPLE G

This example illustrates the preparation of a representative pharmaceutical composition containing a compound of this invention.

A frozen solution suitable for injection is prepared having the following composition:

| Frozen Solution | |
|---|---|
| Active Compound | 250 mg to 1000 mg |
| Hydroxypropyl-β-cyclodextrin | 250 mg to 10 g |
| Excipients-e.g., dextrose | 0–50 g |
| Water for Injection | 10–100 mL |

The weight ratio of hydroxypropyl-β-cyclodextrin to the active compound will typically be from about 1:1 to about 10:1.

Representative Procedure: Hydroxypropyl-β-cyclodextrin and excipients, if any, are dissolved in about 80% of the water for injection and the active compound is added and dissolved. The pH is adjusted with 1 M sodium hydroxide to 4.7±0.3 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

FORMULATION EXAMPLE H

This example illustrates the preparation of a representative pharmaceutical composition containing a compound of this invention.

A lyophilized powder useful for preparing an injectable solution is prepared having the following composition:

| Lyophilized Powder | |
|---|---|
| Active Compound | 250 mg to 1000 mg |
| Hydroxypropyl-β-cyclodextrin | 250 mg to 10 g |
| Excipients-e.g., mannitol, sucrose and/or lactose | 0–50 g |
| Buffer agent-e.g., citrate | 0–500 mg |

The weight ratio of hydroxypropyl-β-cyclodextrin to the active compound will typically be from about 1:1 to about 10:1.

Representative Procedure: Hydroxypropyl-β-cyclodextrin and excipients and/or buffering agents, if any, are dissolved in about 60% of the water for injection. The active compound is added and dissolved and the pH is adjusted with 1 M sodium hydroxide to 4.0–5.0 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored at room temperature or under refrigeration.

FORMULATION EXAMPLE I

This example illustrates the preparation of a representative pharmaceutical composition containing a compound of this invention.

A sterile powder useful for preparing an injectable solution is prepared having the following composition:

| Sterile Powder | |
| --- | --- |
| Active Compound | 250 mg to 1000 mg |
| Hydroxypropyl-β-cyclodextrin | 250 mg to 10 g$^1$ |
| Excipients | optional |

The weight ratio of hydroxypropyl-β-cyclodextrin to the active will typically be from about 1:1 to about 10:1.

Representative Procedure: Hydroxypropyl-β-cyclodextrin and the active compound (and any excipients) are dispersed into an appropriate sterile container and the container is sealed (optionally under partial vacuum or dry nitrogen), labeled and stored at room temperature or under refrigeration.

Administration of Representative Formulations H and I to a Patient

The pharmaceutical formulations described in formulation examples H and I above can be administered intravenously to a patient by the appropriate medical personnel to treat or prevent gram-positive infections. For administration, the above formulations can be reconstituted and/or diluted with a diluent, such as 5% dextrose or sterile saline, as follows:

Representative Procedure: The lyophilized powder of formulation example H (e.g., containing 1000 mg of active compound) is reconstituted with 20 mL of sterile water and the resulting solution is further diluted with 80 mL of sterile saline in a 100 mL infusion bag.

The diluted solution is then administered to the patient intravenously over 30 to 120 minutes.

FORMULATION EXAMPLE J

This example illustrates the preparation of a representative pharmaceutical composition for topical application of a compound of this invention.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE K

This example illustrates the preparation of a representative pharmaceutical composition containing a compound of this invention.

A suppository totaling 2.5 grams is prepared having the following composition:

| Ingredients | |
| --- | --- |
| Active Compound | 500 mg |
| Witepsol H-15* | balance |

*(triglycerides of saturated vegetable fatty acid; a product of Riches-Nelson, Inc., New York, N.Y.)

Utility

The glycopeptide compounds of this invention, and their pharmaceutically acceptable salts, are useful in medical treatments and exhibit biological activity, including antibacterial activity, which can be demonstrated in using the tests described herein. Such tests are well known to those skilled in the art, and are referenced and described in Lorian "Antibiotics in Laboratory Medicine", Fourth Edition, Williams and Wilkins (1991).

Accordingly, this invention provides methods for treating bacterial or infectious diseases, especially those caused by Gram-positive microorganisms, in animals. The compounds of this invention are particularly useful in treating infections caused by methicillin-resistant staphylococci. Also, the compounds are useful in treating infection due to enterococci, including vancomycin-resistant enterococci (VRE). Examples of such diseases include severe staphylococcal infections, such as staphylococcal endocarditis and staphylococcal septicemia. The animal treated may be either susceptible to, or infected with, the microorganism. The method of treatment typically comprises administering to the animal an amount of a compound of this invention which is effective for this purpose.

In practicing this method, the antibiotic can be administered in a single daily dose or in multiple doses per day. The treatment regimen may require administration over extended periods of time, for example, for several days or for from one to six weeks. The amount per administered dose or the total amount administered will depend on such factors as the nature and severity of the infection, the age and general health of the patient, the tolerance of the patient to the antibiotic and the microorganism or microorganisms in the infection.

Among other properties, the glycopeptide compounds of the invention have been found to have reduced mammalian toxicity when administered to a mammal. For example, the polyhydroxy derivatives of the invention have been found to have reduced liver and/or kidney accumulation compared to the corresponding non-phosphono substituted compounds. Moreover, certain compounds of this invention are expected to have reduced nephrotoxicity. Additionally, it has been discovered that the addition of a cyclodextrin compound to a pharmaceutical composition containing the glycopeptide compounds of this invention further reduces the nephrotoxicity and/or tissue accumulation of the glycopeptide compound when administered to a mammal.

The following synthetic and biological examples are offered to illustrate this invention and are not to be construed in any way as limiting the scope of this invention.

EXAMPLES

In the examples below, the following abbreviations have the following meanings. Any abbreviations not defined have their generally accepted meaning. Unless otherwise stated, all temperatures are in degrees Celsius.

| | |
|---|---|
| ACN = | acetonitrile |
| BOC, Boc = | tert-butoxycarbonyl |
| DIBAL-H = | diisobutylaluminum hydride |
| DIPEA = | diisopropylethylamine |
| DMF = | N,N-dimethylformamide |
| DMSO = | dimethyl sulfoxide |
| eq. = | equivalent |
| EtOAc = | ethyl acetate |
| Fmoc = | 9-fluorenylmethoxycarbonyl |
| HOBT = | 1-hydroxybenzotriazole hydrate |
| Me = | methyl |
| PyBOP = | benzotriazol-1-yloxytris(pyrrolidino)phosphonium hexafluorophosphate |
| TEMPO = | 2,2,6,6-tetramethyl-piperidinyloxy, free radical |
| TFA = | trifluoroacetic acid |
| THF = | tetrahydrofuran |
| TLC, tlc = | thin layer chromatography |

In the following examples, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., Milwaukee, Wis. 53201.

General Procedure A

Reductive Alkylation of Vancomycin

To a mixture of vancomycin (1 eq.) and the desired aldehyde (1.3 eq.) in DMF was added DIPEA (2 eq.). The reaction was stirred at ambient temperature for 1–2 hours and monitored by reverse-phase HPLC. Methanol and NaCNBH$_3$ (1 eq.) were added to the solution, followed by TFA (3 eq.). Stirring was continued for an additional hour at ambient temperature. After the reaction was complete, the methanol was removed in vacuo. The residue was precipitated in acetonitrile. Filtration gave the crude product which was then purified by reverse-phase HPLC. If desired, other glycopeptides antibiotics may be used in this procedure.

General Procedure B

Preparation of Dihydroxylated Aldehydes a. Methyl 2-tridecenoate.

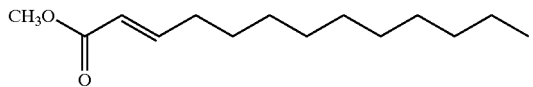

To a suspension of NaH (0.54 g, 13.5 mmol, 1.2 equiv) and DME (45 mL), was added trimethyl phosphonoacetate (2.3 g, 12.4 mmol, 1.1 equiv) in 12 mL of DME, and the resulting mixture was stirred for 30 minutes. The reaction mixture was cooled to 0° C., undecylic aldehyde (1.98 g, 11.3 mmol, 1.0 equiv) was added, the mixture was stirred for 30 minutes, warmed to room temperature, and stirred over night. The reaction was quench with acetic acid, and concentrated. Purification by flash chromatography (SiO$_2$, 3% ethyl acetate/hexanes) gave the desired olefin (1.55 g) as a colorless oil.

b. Methyl 2,3-dihydroxytridecanoate.

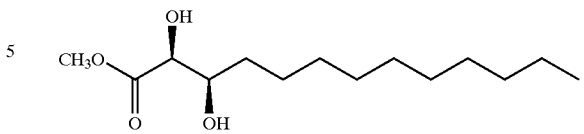

A mixture of AD-mix-β (11.5 g, 1.2 equiv), 40 mL of water, and 40 mL of t-butyl alcohol was stirred at room temperature for 10 minutes to produce two clear phases. Methanesulfonamide (0.65 g, 6.8 mmol, 1.0 equiv) was added, and the mixture was cooled to 0° C. whereupon some of the dissolved salts precipitated. Olefin from the above step (1.55 g, 6.8 mmol, 1.0 equiv) was added at once, and the heterogeneous slurry was stirred vigorously at 0° C. After most of the starting material was consumed (as indicated by TLC), solid sodium sulfite (12.5 g) was added at 0° C., and the mixture was allowed to warm to room temperature and stirred for 1 hour. The reaction mixture was separated, extracted with ethyl acetate. Combined organic layers were washed with 2 N KOH, dried over anhydrous sodium sulfate, and concentrated to provide the diol as a white solid (1.5 g), which was used without further purification.

c. Methyl 2,3-bis(trimethylsilyloxy)tridecanoate

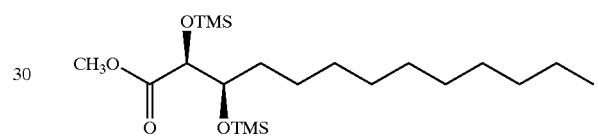

The diol from the above step (1.5 g, 5.8 mmol, 1.0 equiv) was treated with TMS—N(CH$_3$)$_2$ (2.0 mL, 12.1 mmol, 2.1 equiv) at room temperature under N$_2$. After stirring for 4 hours, the reaction mixture was concentrated to give the bis(TMS)diol ester as a white crystalline solid (2.4 g), which was used for next step without purification.

d. 2,3-bis(trimethylsilyloxy)tridecanal

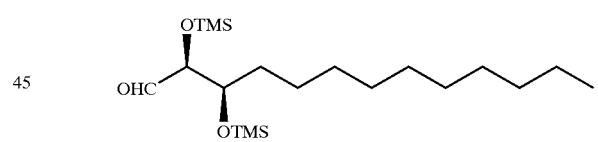

To a solution of the bis(TMS)diol ester from the above step (2.4 g, 5.8 mmol, 1.0 equiv) and 30 mL of ether, at −78° C., was added DIBAL-H (1.0 M in cyclohexane, 8.7 mL, 8.7 mmol, 1.5 equiv) dropwise. After stirring for 3 hours at −78° C., the reaction mixture was quenched with ethyl formate, followed by 10% acetic acid, and warmed to 0° C. Reaction mixture was separated, extracted with ether, dried with MgSO$_4$, and concentrated to provide the aldehyde as a colorless oil (2.3 g), which was used without further purification.

Example 1

General Procedure

Preparation of Dihydroxylated Vancomycin Derivatives (Compound 1, Formula II wherein R$^3$ is OH; R$^5$ is hydrogen; R$^{19}$ is hydrogen, and R$^{20}$ is CH$_3$(CH$_2$)$_9$CH(OH)—CH(OH)CH$_2$—)

To a mixture of vancomycin hydrochloride (5.6 g, 3.8 mmol, 1.0 equiv) and aldehyde from sub-part d above (2.3 g, 5.7 mmol, 1.5 equiv) in 56 mL of DMF was added DIPEA (2.0 mL, 11.4 mmol, 3.0 equiv). The reaction was stirred at room temperature for 2 hours. Methanol (56 mL) and TFA (1.46 mL, 19mmol, 5.0 equiv) was added, followed by NaCNBH$_3$ (0.3 g, 4.6 mmol, 1.2 equiv). Stirring was continued for 2 hours at room temperature. Methanol was then removed using a rotoevaporator. The residue was precipitated in ether. Filtration gave the crude product which was purified by reverse-phase HPLC to give the title compound as a white powder. MS calculated (M+H): 1663.6; found: 1664.6.

Using the above procedures and the appropriate starting materials the compounds shown in Table I were prepared. The mass spectral data for these compounds were as follows:

| Compound No. | MW (freebase) | Observed MH$^+$ |
|---|---|---|
| 1 | 1663.6 | 1664.6 |
| 2 | 1691.7 | |
| 3 | 1709.7 | 1710.7 |
| 4 | 1710.0 | 1710.4 |

Example 2

Determination of Antibacterial Activity

A. In Vitro Determination of Antibacterial Activity

1. Determination of Minimal Inhibitory Concentrations (MICs)

Bacterial strains were obtained from either American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin resistant enterococci were phenotyped as Van A or Van B based on their sensitivity to teicoplanin. Some vancomycin resistant enterococci that had been genotyped as Van A, Van B, Van C1 or Van C2 were obtained from the Mayo Clinic.

Minimal inhibitory concentrations (MICs) were measured in a microdilution broth procedure under NCCLS guidelines. Routinely, the compounds were serially diluted into Mueller-Hinton broth in 96-well microtiter plates. Overnight cultures of bacterial strains were diluted based on absorbance at 600 nm so that the final concentration in each well was 5×10$^5$ cfu/mL. Plates were returned to a 35° C. incubator. The following day (or 24 hours in the case of Enterococci strains), MICs were determined by visual inspection of the plates. Strains routinely tested in the initial screen included methicillin-sensitive *Staphylococcus aureus* (MSSA), methicillin-resistant *Staphylococcus aureus,* methicillin-sensitive *Staphylococcus epidermidis* (MS SE), methicillin-resistant *Staphylococcus epidermidis* (MRSE), vancomycin sensitive *Enterococcus faecium* (VSE Fm), vancomycin sensitive *Enterococcus faecalis* VSE Fs), vancomycin resistant *Enterococcus faecium* also resistant to teicoplanin (VRE Fm Van A), vancomycin resistant *Enterococcus faecium* sensitive to teicoplanin (VRE Fm Van B), vancomycin resistant *Enterococcus faecalis* also resistant to teicoplanin (VRE Fs Van A), vancomycin resistant *Enterococcus faecalis* sensitive to teicoplanin (VRE Fs Van B), enterococcus gallinarium of the Van A genotype (VRE Gm Van A), enterococcus gallinarium of the Van C-1 genotype (VRE Gm Van C-1), enterococcus casseliflavus of the Van C-2 genotype (VRE Cs Van C-2), enterococcus flavescens of the Van C-2 genotype (VRE Fv Van C-2), and penicillin-sensitive Streptococcus pneumoniae (PSSP) and penicillin-resistant Streptococcus pneumoniae (PSRP). Because of the inability of PSSP and PSRP to grow well in Mueller-Hinton broth, MICs with those strains were determined using either TSA broth supplemented with defibrinated blood or blood agar plates. Compounds which had significant activity against the strains mentioned above were then tested for MIC values in a larger panel of clinical isolates including the species listed above as well as non-speciated coagulase negative Staphylococcus both sensitive and resistant to methicillin (MS-CNS and MR-CNS). In addition, they were tested for MICs against gram negative organisms, such as *Escherichia coli* and *Pseudomonas aeruginosa*.

2. Determination of Kill Time

Experiments to determine the time required to kill the bacteria were conducted as described in Lorian, "Antibiotics in Laboratory Medicine", Fourth Edition, Williams and Wilkins (1991). These experiments were conducted normally with both staphylococcus and enterococcus strains.

Briefly, several colonies were selected from an agar plate and grown at 35° C. under constant agitation until it achieved a turbidity of approximately 1.5 and 10$^8$ CFU/mL. The sample was then diluted to about 6×10$^6$ CFU/mL and incubated at 35° C. under constant agitation was continued. At various times aliquots were removed and five ten-fold serial dilutions were performed. The pour plate method was used to determine the number of colony forming units (CFUs).

In general, the compounds of the invention were active in the above tests in vitro tests and demonstrated a broad spectrum of activity.

B. In Vivo Determination of Antibacterial Activity

1. Acute Tolerability Studies in Mice

In these studies, a compound of this invention was administered either intravenously or subcutaneously and observed for 5–15 minutes. If there were no adverse effects, the dose was increased in a second group of mice. This dose incrementation continued until mortality occurred, or the dose was maximized. Generally, dosing began at 20 mg/kg and increased by 20 mg/kg each time until the maximum tolerated dose (MTD) is achieved.

2. Bioavailability Studies in Mice

Mice were administered a compound of this invention either intravenously or subcutaneously at a therapeutic dose (in general, approximately 50 mg/kg). Groups of animals were placed in metabolic cages so that urine and feces could be collected for analysis. Groups of animals (n=3) were sacrificed at various times (10 min, 1 hour and 4 hours). Blood was collected by cardiac puncture and the following organs were harvested—lung, liver, heart, brain, kidney, and spleen. Tissues were weighed and prepared for HPLC analysis. HPLC analysis on the tissue homogenates and fluids was used to determine the concentration of the test compound or Iil present. Metabolic products resulting from changes to the test compound were also determined at this juncture.

3. Mouse Septicemia Model

In this model, an appropriately virulent strain of bacteria (most commonly *S. aureus,* or *E. Faecalis* or *E. Faecium*) was administered to mice (N=5 to 10 mice per group) intraperitoneally. The bacteria was combined with hog gastric mucin to enhance virulence. The dose of bacteria (normally $10^5$–$10^7$) was that sufficient to induce mortality in all of the mice over a three day period. One hour after the bacteria was administered, a compound of this invention was administered in a single dose either IV or subcutaneously. Each dose was administered to groups of 5 to 10 mice, at doses that typically ranged from a maximum of about 20 mg/kg to a minimum of less than 1 mg/kg. A positive control (normally vancomycin with vancomycin sensitive strains) was administered in each experiment. The dose at which approximately 50% of the animals are saved was calculated from the results.

4. Neutropenic Thigh Model

In this model, antibacterial activity of a compound of this invention was evaluated against an appropriately virulent strain of bacteria (most commonly *S. aureus,* or *E. Faecalis* or *E. Faecium,* sensitive or resistant to vancomycin). Mice were initially rendered neutropenic by administration of cyclophosphamide at 200 mg/kg on day 0 and day 2. On day 4 they were infected in the left anterior thigh by an IM injection of a single dose of bacteria. The mice were then administered the test compound one hour after the bacteria and at various later times (normally 1, 2.5, 4 and 24 hours) the mice were sacrificed (3 per time point) and the thigh excised, homogenized and the number of CFUs (colony forming units) were determined by plating. Blood was also plated to determine the CFUs in the blood.

5. Pharmacokinetic Studies

The rate at which a compound of this invention is removed from the blood can be determined in either rats or mice. In rats, the test animals were cannulated in the jugular vein. The test compound was administered via tail vein injection, and at various time points (normally 5, 15, 30,60 minutes and 2,4,6 and 24 hours) blood was withdrawn from the cannula In mice, the test compound was also administered via tail vein injection, and at various time points. Blood was normally obtained by cardiac puncture. The concentration of the remaining test compound was determined by HPLC.

In general, the compounds of the invention were active in the above test in vivo and demonstrated a broad spectrum of activity.

Example 3

Determination of Tissue Accumulation

A. Tissue Distribution Using Radiolabeled Compound

This procedure is used to examine the tissue distribution, excretion and metabolism of a radiolabeled test compound in both male and female rats following intravenous infusion at 10 mg/kg. Male and female Sprague-Dawley rats (n=2 per sex per compound) are dosed with $^3$H-labeled test compound at 10 (400 µCi/kg) and 12.5 mg/kg (100 µCi/kg), respectively, via intravenous infusion (~2 min). The test compound is formulated in 5% hydroxypropyl-β-cyclodextrin as 2.5 mg/mL solution. Urine and feces are cage collected over 24 hours period. At 24 hours after dosing, animals are sacrificed and tissues are removed. Serum, urine and tissues are analyzed for total radioactivity by oxidation followed by liquid scintillation counting. Urine and selected tissues samples are extracted and analyzed by reverse phase HPLC with radioactive flow detector for the presence of potential metabolites.

B. Tissue Accumulation Following Single Dose

This procedure is used to evaluate tissue distribution of a test compound in rats following single dose administration by infusion. Male Sprague-Dawley rats (n=3 per dose groups) are dosed with 50 mg/kg of a test compound. Two formulations are used: 30% PEG 400 and 10% sulfobutylether-β-cyclodextrin. Urine samples are cage collected over 24 hours. Blood samples are collected for serum chemistry and concentration determination. Liver and kidneys are removed for histology evaluation. One kidney and part of the liver are homogenized for concentration analysis using reverse phase HPLC with UV detection. Drug concentrations in urine and serum samples are determined by LC-MS analysis.

C. Tissue Distribution Following Multiple Doses

This procedure is used too evaluate the potential tissue accumulation of a test compound in rats following multiple dose administration by intravenous infusion. Male and female Sprague-Dawley rats (n=4 per sex per dose group) are dosed with a test compound at 12.5, 25 and 50 mg/kg per day for seven days. Animals are sacrificed at day 1 (n=3 per sex per dose group) following the last dose administered. One animal per sex per dose group is retained as recovery animal and sacrificed at day 7 following the last dose administered. The test compound is formulated in 5% hydroxypropyl-β-cyclodextrin or 1% sucrose/4.5% dextrose. Urine samples are cage collected at days 1 and 7 post-dose. Blood samples are collected for serum chemistry and concentration determination. Liver and kidneys are removed for histology evaluation. One kidney and part of the liver are homogenized for concentration analysis using reverse phase HPLC with UV detection. Drug concentrations in urine and serum samples are determined by LC-MS analysis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in fill, as though individually incorporated by reference.

What is claimed is:

1. A modified glycopeptide of formula II:

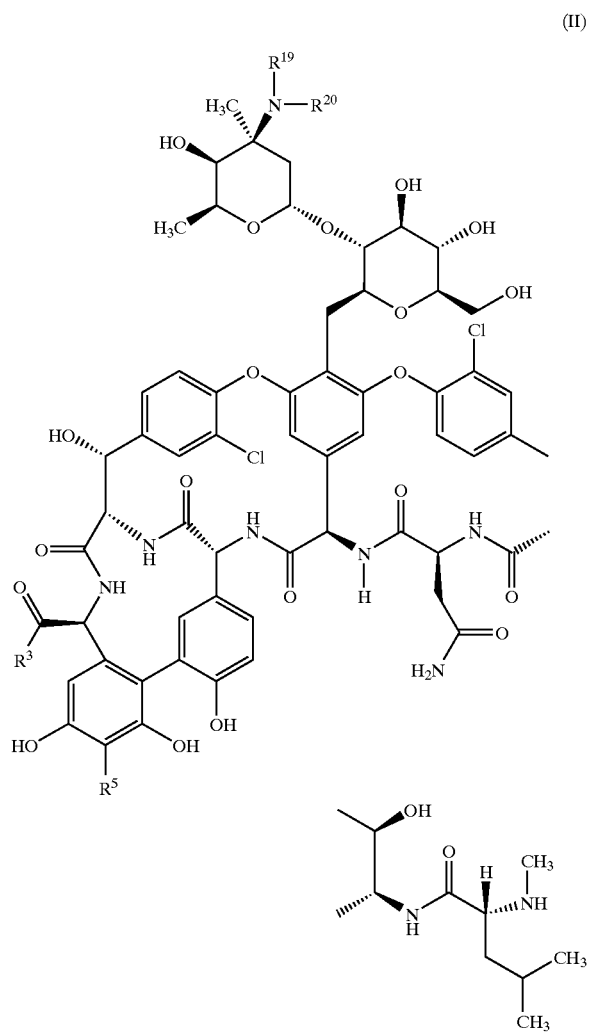

(II)

wherein:
R$^3$ is —OH;
R$^5$ is hydrogen;
R$^{19}$ is hydrogen;
R$^{20}$ is —CH$_2$—CH(OH)CH(OH)CH$_2$—Y—R$^b$(Z)$_x$ or —CH$_2$—CH(OH)CH(OH)CH$_2$—R$^{17}$;
within R$^{20}$ moiety R$^{17}$ is hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl or heterocyclic;
within moiety R$^{20}$ Y is selected from the group consisting of oxygen, sulfur, —S—S—, NR$^c$—, —S(O)—, —SO$_2$—, —NR$^c$C(O)—, —OSO$_2$—, —OC(O)—, —NR$^c$SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(=O)—and —NR$^c$SO$_2$NR$^c$—;
within R$^{20}$ moiety each Z is independently selected from the group consisting of hydrogen, aryl, cycloalkyl, cycloalkenyl, heteroaryl and heterocyclic and x is 1 or 2;

within Y moiety R$^b$ is selected from the group consisting of a covalent bond, alkylene, substituted alkylene, alkenylene, substituted alkenylene, alkynylene and substituted alkynylene, provided R$^b$ is not a covalent bond when Z is hydrogen;
each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;
within R$^c$ moiety each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; and or a pharmaceutically acceptable salt or a stereoisomer thereof.

2. A pharmaceutical composition comprising a pharmaceutically acceptable carrier and a therapeutically effective amount of a compound of claim 1.

3. The pharmaceutical composition of claim 2, wherein the composition further comprises a cyclodextrin.

4. The glycopeptide of claim 1, wherein R$^{20}$ is —CH$_2$—CH(OH)CH(OH)CH$_2$—R$^{17}$ and R$^{17}$ is alkyl.

5. The glycopeptide of claim 1, wherein R$^{20}$ is —CH$_2$—CH(OH)CH(OH)CH$_2$—R$^{17}$ and R$^{17}$ is aryl.

6. The glycopeptide of claim 1, wherein R$^{20}$ is —CH$_2$—CH(OH)CH(OH)CH$_2$—Y—R$^b$—(Z)$_x$ and Y is an —NH— group Z is independently selected from the group consisting of hydrogen, aryl, cycloalkyl, cycloalkenyl, heteroaryl and heterocyclic; and x is 1 or 2.

7. The glycopeptide of claim 1, wherein R$^{20}$ is —CH$_2$—CH(OH)CH(OH)CH$_2$—Y—R$^b$—(Z)$_x$ and Y is oxygen Z is independently selected from the group consisting of hydrogen, aryl, cycloalkyl, cycloalkenyl, heteroaryl and heterocyclic; and x is 1 or 2.

8. The glycopeptide of claim 1, wherein R$^{20}$ is —CH$_2$—CH(OH)CH(OH)CH$_2$—Y—R$^b$—(Z)$_x$ and Y is sulfur Z is independently selected from the group consisting of hydrogen, aryl, cycloalkyl, cycloalkenyl, heteroaryl and heterocyclic; and x is 1 or 2.

9. The glycopeptide of claim 1, wherein R$^{20}$ is —CH$_2$—CH(OH)CH(OH)CH$_2$—Y—R$^b$—(Z)$_x$ and R$^b$ is alkylene Z is independently selected from the group consisting of hydrogen, aryl, cycloalkyl, cycloalkenyl, heteroaryl and heterocyclic; and x is 1 or 2.

10. The glycopeptide of claim 1, wherein R$^{20}$ is —CH$_2$—CH(OH)CH(OH)CH$_2$—Y—R$^b$—(Z)$_x$ and Z is hydrogen and x is 1 or 2.

11. The glycopeptide of claim 1, wherein R$^{20}$ has the structure:

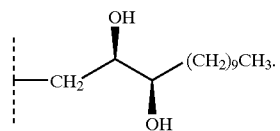

12. The glycopeptide of claim 1, wherein $R^{20}$ has the structure:

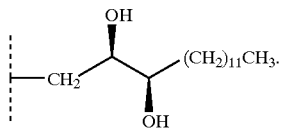

13. The glycopeptide of claim 1, wherein $R^{20}$ has the structure:

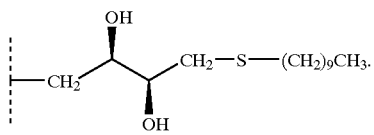

14. The glycopeptide of claim 1, wherein $R^{20}$ has the structure:

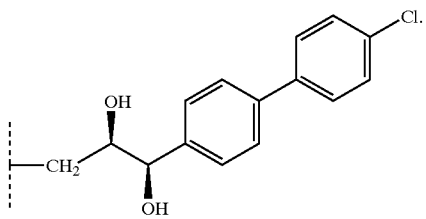

15. A method of treating a bacterial disease in a mammal comprising administering to the mammal a therapeutically effective amount of a glycopeptide of claim 1.

16. A method of treating a bacterial disease in a mammal comprising administering to the mammal a therapeutically effective amount of a pharmaceutical composition of claim 2.

* * * * *

UNITED STATES PATENT AND TRADEMARK OFFICE
CERTIFICATE OF CORRECTION

PATENT NO. : 6,828,299 B2
DATED : December 7, 2004
INVENTOR(S) : Yang et al.

It is certified that error appears in the above-identified patent and that said Letters Patent is hereby corrected as shown below:

Column 39,
Lines 5-42, replace the structure of formula (II) with the following structure:

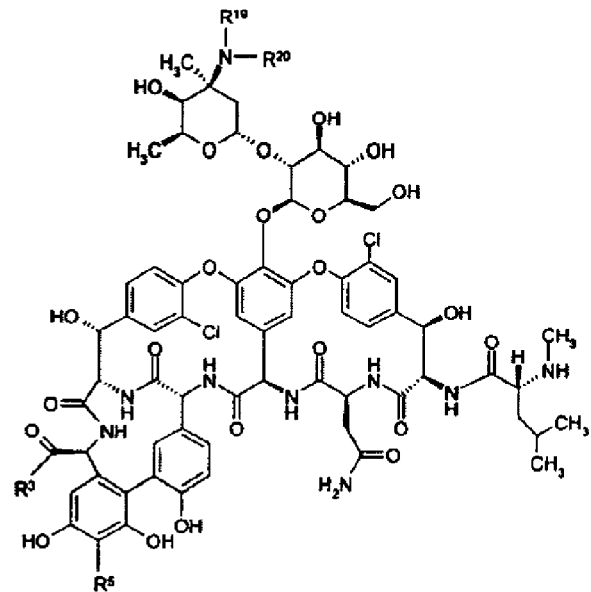

Line 56, replace "$NR^c$-" with -- $NR^c$- --.

Signed and Sealed this

Twenty-second Day of March, 2005

JON W. DUDAS
*Director of the United States Patent and Trademark Office*